United States Patent
Weaver (10) Patent No.: US 10,330,209 B2
(45) Date of Patent: Jun. 25, 2019

(54) CHECK VALVE AND METHOD OF FORMING A CHECK VALVE

(71) Applicant: Fresenius Medical Care Holdings, Inc., Waltham, MA (US)

(72) Inventor: Colin Weaver, Pleasanton, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 6 days.

(21) Appl. No.: 15/416,427

(22) Filed: Jan. 26, 2017

(65) Prior Publication Data

US 2018/0209553 A1    Jul. 26, 2018

(51) Int. Cl.
| | |
|---|---|
| *F16K 15/02* | (2006.01) |
| *F16K 31/122* | (2006.01) |
| *A61M 1/14* | (2006.01) |
| *A61M 39/24* | (2006.01) |
| *F16K 15/06* | (2006.01) |
| *F16K 27/02* | (2006.01) |

(52) U.S. Cl.
CPC ............ *F16K 15/021* (2013.01); *A61M 1/14* (2013.01); *A61M 39/24* (2013.01); *F16K 15/063* (2013.01); *F16K 27/0209* (2013.01); *F16K 31/1221* (2013.01)

(58) Field of Classification Search
CPC .......................... F16K 15/021; F16K 31/1221
USPC .......................................................... 137/541
See application file for complete search history.

(56) References Cited

U.S. PATENT DOCUMENTS

| | | | |
|---|---|---|---|
| 1,779,421 A | 10/1930 | Cox | |
| 2,809,660 A | 10/1957 | Becker | |
| 2,912,002 A | 11/1959 | Miller | |
| 3,590,851 A * | 7/1971 | Bogossian | F16K 15/20 |
| | | | 137/223 |
| 3,735,777 A | 5/1973 | Katzer et al. | |
| 3,741,243 A | 6/1973 | Deibler et al. | |
| 3,889,879 A | 6/1975 | Wellman et al. | |
| 4,051,007 A | 9/1977 | Hossle | |
| 4,129,145 A | 12/1978 | Wynn | |
| 4,415,027 A | 11/1983 | Russell | |
| 4,506,695 A * | 3/1985 | Kuypers | B60C 29/02 |
| | | | 137/223 |
| 4,556,195 A | 12/1985 | Calkins | |
| 4,892,706 A | 1/1990 | Kralovic et al. | |
| 5,542,681 A | 8/1996 | Hutchens et al. | |
| 6,105,645 A * | 8/2000 | Ingram | B60C 23/003 |
| | | | 152/415 |

(Continued)

FOREIGN PATENT DOCUMENTS

| | | |
|---|---|---|
| CN | 201460812 U | 5/2010 |
| CN | 202349291 U | 7/2012 |

(Continued)

OTHER PUBLICATIONS

International Search Report and Written Opinion dated Apr. 30, 2018, for PCT/US18/15234 (14 pages).

*Primary Examiner* — P. Macade Nichols (57) ABSTRACT

A check valve includes a hollow body. The hollow body includes an inlet end and an outlet end, the inlet end having a first connector and the outlet end having a second connector. A connecting projection is disposed along a length of an outer surface. A protrusion extends from the outer surface, the protrusion corresponding to a direction of fluid flow.

19 Claims, 6 Drawing Sheets

(56) References Cited

U.S. PATENT DOCUMENTS

| | | | |
|---|---|---|---|
| 6,231,085 B1 | 5/2001 | Olson | |
| 6,871,507 B1 | 3/2005 | Goldsmith | |
| 8,596,560 B2 | 12/2013 | Morgan et al. | |
| 9,279,515 B2 | 3/2016 | Broderick | |
| 2002/0170603 A1* | 11/2002 | Cerovich | F04B 39/102 |
| | | | 137/514 |
| 2005/0263187 A1 | 12/2005 | Jernigan et al. | |
| 2010/0006159 A1* | 1/2010 | Lin | F16K 15/063 |
| | | | 137/491 |
| 2015/0159591 A1 | 6/2015 | Hambloch et al. | |

FOREIGN PATENT DOCUMENTS

| | | |
|---|---|---|
| CN | 204344962 U | 5/2015 |
| CN | 204358187 U | 5/2015 |
| EP | 1582264 B1 | 8/2011 |
| GB | 2386392 A | 9/2003 |

\* cited by examiner

CHECK VALVE AND METHOD OF FORMING A CHECK VALVE

FIELD OF THE DISCLOSURE

The disclosure generally relates to a check valve, and more particularly to a single body check valve for use in a hemodialysis device.

BACKGROUND OF THE INVENTION

Medical devices involving fluid flow typically include check valves to ensure proper functioning. A hemodialysis device can function in place of a kidney by filtering waste, salt, and fluid from a patient's blood when the patient's kidneys do not function properly. A fluid flow path in a hemodialysis device may include one or more check valves to ensure proper fluid flow through the device. However, the check valves are subjected to high temperatures of up to 90° C., and a high pressure pulsating fluid flow of approximately 12,000,000 cycles per year at approximately 15 psi every 1.1 seconds. Additionally, the fluid contents may be corrosive, including salt water, bleach, acetic acid, paracetic acid, and citric acid.

Known check valves are unable to withstand this harsh environment for long periods of time, requiring frequent replacement. The hemodialysis device must then be taken out of service for maintenance. When the check valve is replaced, a user must be able to quickly and correctly align it properly in the fluid flow path. However, symmetrical check valves make it difficult for users to determine correct alignment, and markings that may be on a check valve are difficult to see in working conditions. If installed improperly, the device may require additional maintenance downtime for corrections.

Additionally, corrosive fluid flowing through the check valve can cause components to corrode and prematurely fail. For example, a spring and poppet assembly in the check valve maintains the seal in the check valve. Over time valve assembly components may corrode, affecting the sealing capability of the check valve. The fluid flow may also cause particulate build-up at the valve seat, which over time may also affect the sealing capability of the check valve. Valve bodies may also comprise multiple pieces which introduce multiple points where leakage can occur should components of the valve fail. When the check valve can no longer seal and prevent fluid backflow and/or leakage occurs, replacement is necessary.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In an embodiment, a check valve comprises a hollow body, the hollow body including an inlet end and an outlet end, the inlet end having a first connector and the outlet end having a second connector. The hollow body may further include a connecting projection disposed along a length of an outer surface, and a protrusion extending from the outer surface, the protrusion corresponding to a direction of fluid flow.

In an embodiment, a check valve comprises a single piece hollow body configured for a fluid flow from an inlet end to an outlet end, the outlet end including a valve seat on an inner surface. The check valve may further include a spring disposed in the single piece hollow body, and a poppet disposed in the single piece hollow body, the poppet having a first end coupled to the spring and a second end disposed at the valve seat, the poppet extending coaxial to the spring such that the poppet is held in tension by the spring. The check valve may further include a sacrificial anode washer disposed at an end of the spring, the sacrificial anode washer being configured to corrode at a rate faster than the spring, an o-ring disposed at the valve seat and coupled to the second end of the poppet, wherein the single piece hollow body includes a connecting projection disposed along a length of an outer surface.

In an embodiment, a method for forming a check valve comprises forming a single piece hollow body, the single piece hollow body including an inlet end and an outlet end, the inlet end having a first connector and the outlet end having a second connector. The single piece hollow body may further include a connecting projection disposed along a length of an outer surface, and a protrusion on the outer surface, the protrusion corresponding to a direction of fluid flow. The method may further comprise inserting a valve assembly within the hollow body, the valve assembly including a poppet, a spring, and an o-ring.

In an embodiment, a method of operating a check valve comprises inserting the check valve in a flow path, the check valve including a single piece hollow body, the single piece hollow body including an inlet end and an outlet end, the inlet end having a first connector and the outlet end having a second connector. The single piece hollow body may further include a connecting projection disposed along a length of an outer surface and a protrusion extending from the outer surface, the protrusion corresponding to a direction of fluid flow. The method may further comprise positioning the check valve in the flow path such that the protrusion is aligned to indicate the direction of fluid flow in the flow path. The method may further comprise securing the check valve to tubing at the inlet end and the outlet end by inserting the first connector at the inlet end and the second connector at the outlet end, and rotating the tubing to engage with the connecting projection.

BRIEF DESCRIPTION OF THE DRAWINGS

By way of example, specific embodiments of the disclosed device will now be described, with reference to the accompanying drawings, in which.

DETAILED DESCRIPTION

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Figure 1A:
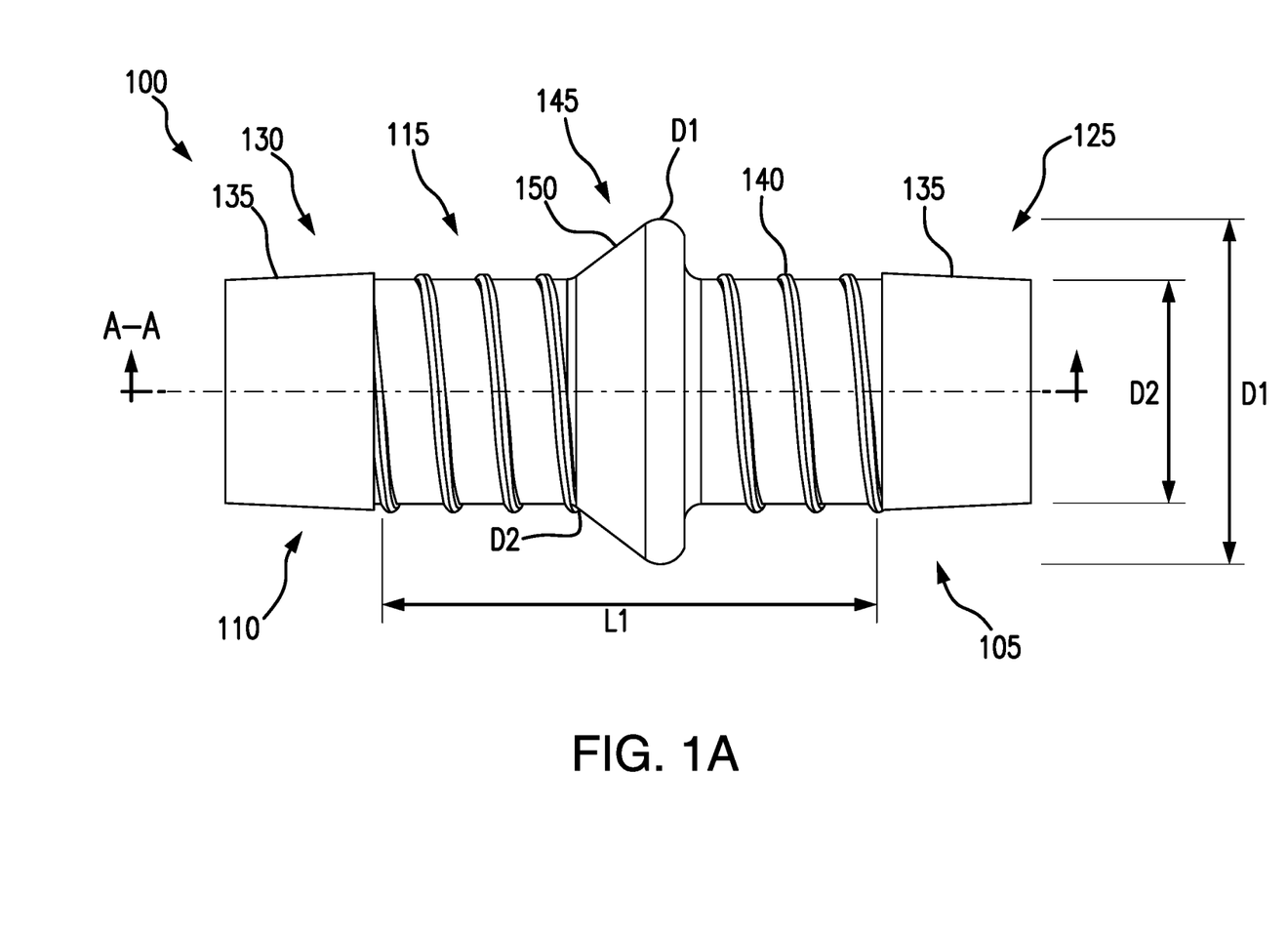
FIG. 1A illustrates a front view of a check valve body according to an embodiment of the present invention.
Figure 1B:
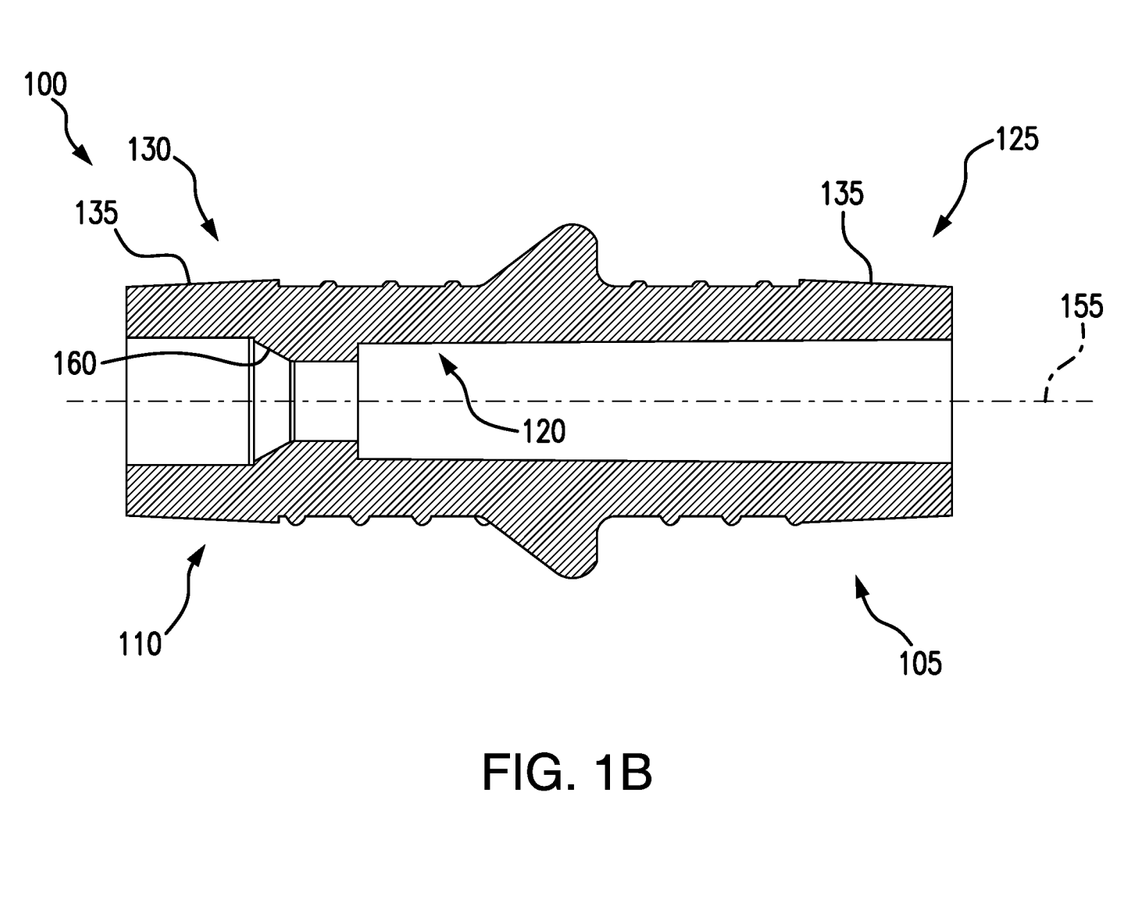
FIG. 1B illustrates a sectional view of a check valve body according to an embodiment of the present invention.

Referring to FIGS. 1A, 1B, a check valve body 100 according to an embodiment of the present invention is shown. FIG. 1A shows a front view of the check valve body 100, which may be a cylindrical hollow body. FIG. 1B is a sectional view A-A of FIG. 1A, which shows the internal portion of the cylindrical hollow body. The check valve body 100 may be a single piece, in that the connecting elements, described more fully below, are integrally formed as part of the check valve body 100. The check valve body 100 may be formed by injection molding a plastic material, including but not limited to PVC. In embodiments, the check valve body 100 may be formed by milling and turning of a metal or metal alloy, including but not limited to titanium and stainless steel.

The check valve body 100 may include an inlet end 105 and an outlet end 110. A direction of fluid flows from the inlet end 105 to the outlet end 110. The check valve body 100 may include an outer surface 115 and an inner surface 120. The outer surface 115 may include a first connector 125 at the inlet end 105 of the body 100 and a second connector 130 at the outlet end 110 of the body 100. The first connector 125 and the second connector 130 may be configured as projections on the outer surface 115 of the check valve body 100, aligned coaxially to the check valve body 100 along longitudinal axis 155. The first connector 125 and the second connector 130 may be configured to secure the check valve body 100 to tubing (not shown). For example, the first connector 125 and the second connector 130 may be one or more barbs, which is a projection having an angled surface 135 increasing in diameter away from an insertion point, so that the check valve may be securely coupled to the tubing. The projection may have a tapered outer surface extending from the outer surface of the hollow body 100. The first connector 125 and the second connector 130 may be a single barb, or a plurality of barbs coaxially aligned with each other, although other known connecting features to secure the check valve body 100 to the tubing are also envisioned. The angled surface 135 may be any angle to securely couple the check valve body 100 to tubing, for example, an end of a first tubing is attached to one of the first or second connector 125, 130, and an end of a second tubing is attached to the other of the first or second connector 125, 130.

The outer surface 115 may further include one or more connecting projections 140 for additional connection. The connecting projection 140 may be a single projection extending along a length L1 of the outer surface 115 of the check valve body 100, the connecting projection extending out of the outer surface 115. In an embodiment, the connecting projection 140 may be helical, and configured to secure to tubing (not shown). In an embodiment, the connecting projection 140 may be a self-tapping screw thread. The self-tapping screw thread may be deforming when connecting to tubing, so that a thread is formed in the tubing as it is rotated together with the screw thread, further securing the check valve body 100 to the tubing. In embodiments, the self-tapping, or thread-forming, screw may only deform but not cut the tubing. Cutting the tubing is disadvantageous as it may result in leakage. The self-tapping screw thread is advantageous over known connecting features in that it allows for easy installation and removal from the hemodialysis device in a user-friendly manner, reducing downtime for device maintenance. The thread 140 may extend along a length L1 of the check valve body 100, up to the first connector 125 and the second connector 130. It is understood that the angled surface 135 of the connector 125, 130 projects beyond a diameter D3 of the thread 140. The tubing may be of a diameter slightly smaller than the maximum diameter D4 of the angled surface 135 of the connectors 125, 130 so that the tubing provides a secure connection with the check valve. Since the tubing is flexible, the tubing will expand radially to receive the connectors 125, 130, and contract to fit around thread 140. In this manner, the thread 140 may deform the tubing to couple with the check valve.

The outer surface 115 may further include a protrusion 145, which is shaped to indicate a flow direction from the inlet end 105 to the outlet end 110. In embodiments, the protrusion 145 may be a flange. In embodiments, the protrusion 145 may be a frustoconical shape protrusion, in that a conical surface 150 indicates the fluid flow direction. The protrusion 145 may have a first diameter D1 disposed towards the inlet end 105 and a second diameter D2 disposed towards the outlet end 110. The first diameter D1 may be larger than the second diameter D2, so that the conical surface indicates the fluid flow direction from the inlet end 105 to the outlet end 110 of the check valve body, e.g., as an arrow.

The protrusion 145 may provide an asymmetry to the check valve body 100, so that a user may quickly determine proper alignment for assembly in a fluid flow path. The asymmetry may be along the longitudinal axis 155, such that the inlet end 105 is easily discernible to a user from the outlet end 110, for ease of assembly. The protrusion 145 may provide a user-friendly visual indicator as to the flow direction, so that a user is aware of the inlet end and the outlet end for proper installation in a hemodialysis device. The protrusion 145 provides a user-friendly indicator on the check valve body 100 to mistake-proof installation, and eliminates the need for additional visual aids such as flashlights and magnifying glasses to see a surface marking. A more user-friendly indicator reduces installation time and opportunity for installation errors and potentially additional device maintenance.

A single piece hollow body as the check valve body 100 may allow for the connecting features to be integrally formed in the body. Thus, the first connector 125, the second connector 130, and the connecting projection 140 may all be formed as part of the check valve body 100. The single piece configuration is advantageous in that it eliminates connection points, which have potential for leaks. For example, a multi-piece configuration may deform over time, reducing alignment and increasing the likelihood of leakage. Once a leak is detected, the hemodialysis device is taken out of service for maintenance and check valve replacement.

Referring to FIG. 1B, a sectional view of the check valve body 100 is shown. An inner surface 120 of the check valve body 100 provides for a fluid flow path from the inlet end 105 to the outlet end 110. As described above, the check valve body 100 may be a cylindrical hollow body having a longitudinal axis 155. The inner surface 120 may include a valve seat 160 at the outlet end 110 of the check valve body 100. As will be described in more detail below, the valve seat 160 is configured to seal the check valve to prevent fluid backflow.

Figure 1C:
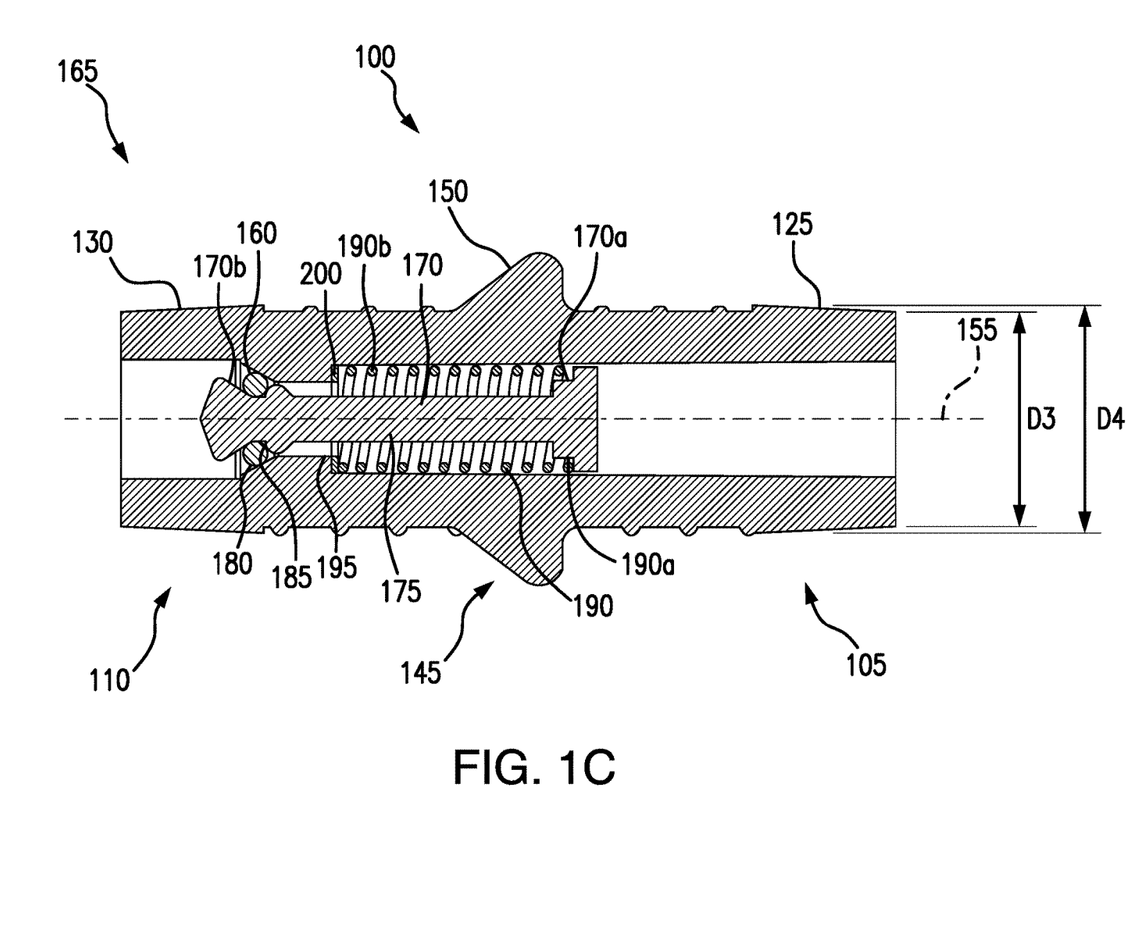
FIG. 1C illustrates a sectional view of a check valve according to an embodiment of the present invention.
Figure 2A:
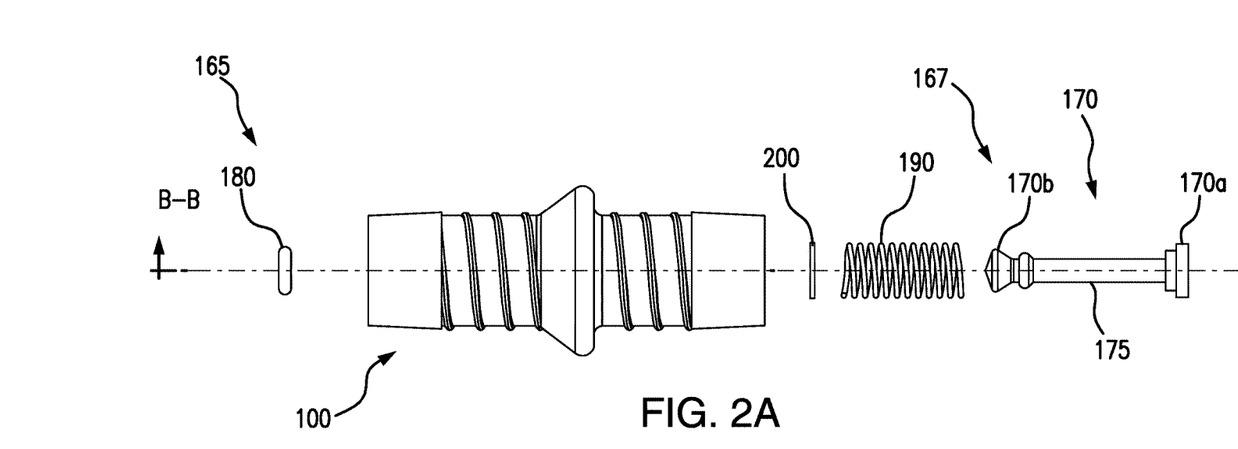
FIGS. 2A, 2B illustrate an exploded front view and a sectional view of a check valve according to an embodiment of the present invention.
Figure 2B:
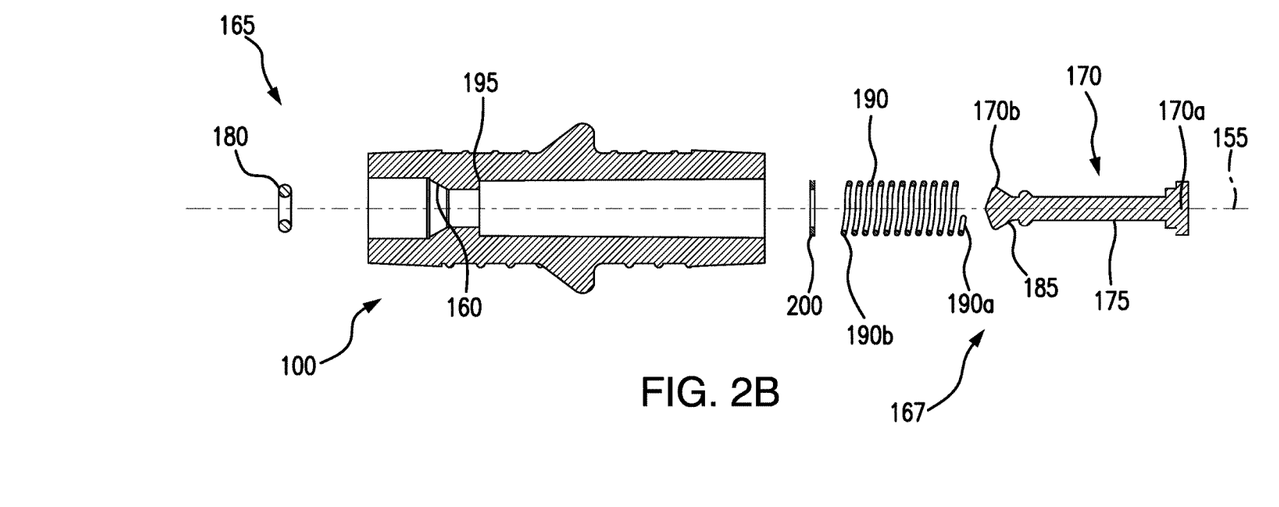

Referring to FIGS. 1C, 2A, and 2B, a check valve 165 is shown in assembled and exploded views. FIG. 2B is a sectional view B-B of FIG. 2A. A valve assembly 167 may be disposed in the check valve body 100, including a poppet 170 having a first end 170a, a second end 170b, and a poppet body 175. The poppet body 175 may extend along the longitudinal axis 155 within the check valve body 100. The first end 170a of the poppet is disposed towards the inlet end 105, and the second end 170b of the poppet is disposed towards the outlet end 110. In embodiments, the second end 170b of the poppet may be disposed at the valve seat 160. The poppet 170 may be made of a material to resist corrosion. The poppet 170 may be made of a metal or metal alloy, e.g., titanium.

The valve assembly 167 may further include an o-ring 180 coupled to the second end 170b of the poppet 170. The second end 170b of the poppet 170 may be configured so that the o-ring 180 seals at the valve seat 160. For example, the o-ring 180 may be coupled in a curvature 185 of the second end 170b of the poppet 170, so that the o-ring is securely coupled to the poppet 170. The o-ring 180 may be coaxial with the poppet 170 when assembled, along the longitudinal axis 155. The o-ring may be made of a plastic material to seal the valve seat 160 by the second end 170b of the poppet 170, for example, an elastomer or silicone, such as EPDM.

The valve assembly 167 may further include a spring 190. Spring 190 may include a first end 190a and a second end 190b disposed along the longitudinal axis 155 inside the check valve body 100 and surrounding the poppet body 175. In an embodiment, the spring 190 is a helical spring. In an embodiment, the spring 190 may be made of a material that resists corrosion. In some embodiments, the spring 190 may be made of a metal or metal alloy, e.g., titanium. The first end 190a of the spring 190 may be coupled to the first end 170a of the poppet 170 towards the inlet end 105 of the check valve body 100, such that the poppet body 175 extends within the coils of the spring 190 as illustrated in FIG. 1C, and the poppet 170 and the spring 190 are coaxial. The spring may be disposed along the longitudinal axis 155. The second end 190b of the spring 190 may be disposed towards the outlet end 110 of the check valve body 100, on a ledge 195 extending inward from the inner surface 120 of the check valve body 100. Ledge 195 may be a stepped surface on the inner surface 120. The second end 170b of the poppet 170 may extend beyond the second end 190b of the spring 190, such that the valve seat 160 is closer to the outlet end than the ledge 195.

The spring 190 may be held between the first end 170a of the poppet 170 and the ledge 195 so that the poppet 170 is held in tension. In embodiments, the tension and/or compression of the spring determines the poppet 170 position relative to the check valve body 100. In an embodiment, the valve assembly 167 maintains the o-ring 180 to seal the valve seat 160 by the spring 190 holding the poppet 170 in tension, thereby preventing fluid backflow.

In an embodiment, the valve assembly 167 may further include a sacrificial anode 200. A sacrificial anode 200 may be disposed in the check valve body 100. Fluid in a hemodialysis device may contain salts and acids in the fluid, which corrodes valve assembly components over time. As described above, components in existing check valves, e.g., the spring, corrode over time from the fluid flow. A sacrificial anode may be included in the valve assembly 167 so that corrosion occurs on the sacrificial anode instead of the valve assembly components, thereby protecting the necessary components from deterioration and failure.

A ring, or washer, may be formed as the sacrificial anode, e.g., formed of a material being lower in Galvanic series than a material of a cathode spring 190. In embodiments, the sacrificial anode may be any shape fitting in the check valve body 100. Thus, the spring 190 is formed of a different material than the sacrificial anode washer 200. This ensures that the washer 200 will corrode before the spring 190, extending the life of the check valve 165. For example, if the poppet 170 and the spring 190 are made of titanium, the washer 200 may be made of a different metal or metal alloy, e.g., stainless steel, or a less corrosive material being lower on the Galvanic series than the material of the spring.

In an embodiment, the sacrificial anode washer 200 may be disposed between the ledge 195 and the second end 190b of the spring 190, although it is envisioned that the sacrificial anode washer 200 may be disposed anywhere within the hollow cylindrical body of the check valve body 100. The washer 200 may be aligned coaxially with the components of the valve assembly 167, along longitudinal axis 155.

In an embodiment, a washer 200 is not included in the system, and the poppet 170 is made to be "sacrificial." For example, the poppet 170 is made of a material being lower in Galvanic series than the spring 190, so the poppet 170 will corrode before the spring 190. In an embodiment, the spring 190 may be made of titanium and the poppet 170 may be made of stainless steel. The poppet 170 may corrode before the spring 190 while still extending the overall life of the check valve 165 because the poppet 170 is free of the system stress that the spring 190 is under.

Figure 3:
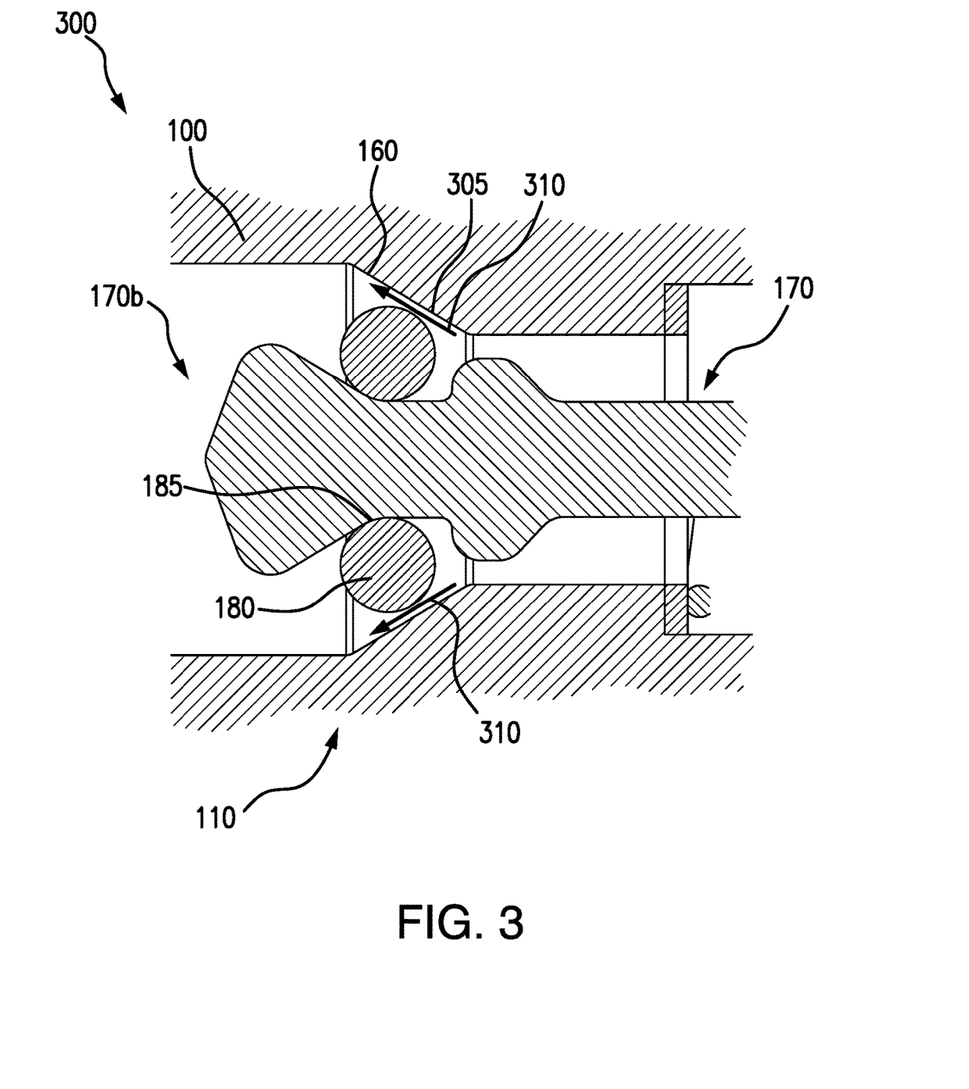
FIG. 3 illustrates a sectional view of a valve seat and o-ring of a check valve according to an embodiment of the present invention.

Referring now to FIG. 3, a portion of the check valve is illustrated as reference numeral 300. As described above, the outlet end 110 includes a second end 170b of the poppet 170, an o-ring 180 coupled to the second end 170b of the poppet 170, disposed at the valve seat 160. The second end 170b of the poppet 170 may be configured to receive the o-ring 180, for example, including a curvature 185 to receive the o-ring 180, such that the o-ring 180 is securely coupled to the poppet 170 and not detachable. The valve seat 160 may include an angled surface 305 extending outward on the inner surface 120. The o-ring 180 may be configured to seal the valve seat 160 at the angled surface 305 when the spring 190 holds the poppet 170 in tension.

When pressure of the fluid flow exceeds the tension of the spring 190, it may compress, so that the poppet 170 is pushed in a direction towards the outlet end 110. The second end 170b of the poppet 170 and the o-ring may thereby become unseated, or unsealed, creating a gap between the valve seat 160 and the o-ring 180 so that fluid may flow out of the outlet end 110, indicated by arrows 310. During operation, the fluid flow pressure may overcome the spring constant in quick bursts to create a small opening, so that the poppet 170 and o-ring 180 are unsealed from the valve seat 160 briefly. Fluid may flow out of the outlet end 110 at a high pressure through the small, restricted opening in response to the poppet 170 and o-ring 180 being unseated, or unsealed. Due to the configuration of the o-ring with respect to the angled surface 305 of the valve seat 160 and the poppet 170, this may result in the fluid flow to exit the outlet end 110 as quick spray bursts. When the fluid flow spray exits the outlet end 110, the higher pressure of the spray may dislodge and flush out particulate build-up on the inner surface 120, in a self-cleaning manner. This is advantageous over known check valves which do not generate a spray of fluid flow as known check valves are typically sized to allow for an unrestricted fluid flow at the outlet when opened, which may allow for salt and other particulates to build-up in the valve seat and potentially affect the sealing capability of the valve assembly.

Figure 4:
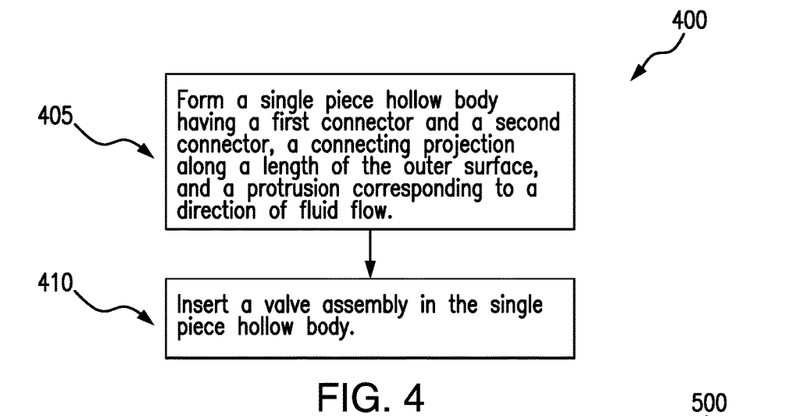
FIG. 4 illustrates a flow diagram of a method of forming a check valve according to an embodiment of the present invention.

FIG. 4 shows a flow diagram 400 of a method of forming a check valve according to an embodiment of the invention. At step 405 the method may include forming a single piece hollow body. The single piece hollow body may include an inlet end and an outlet end, the inlet end having a first connector and the outlet end having a second connector. The single piece hollow body may further include a connecting projection disposed along a length of an outer surface, and a protrusion on the outer surface, the protrusion corresponding to a direction of fluid flow. At step 410, a valve assembly is inserted within the hollow body, which may include a poppet, a spring, and an o-ring.

The poppet may be inserted in the hollow body, the poppet having a first end disposed towards the inlet end, a second disposed at a valve seat in an inner surface of the hollow body, and a poppet body extending between the first end of the poppet and the second end of the poppet. The spring may be inserted in the hollow body, a first end being coupled to the first end of the poppet. A second end of the spring may be disposed on a ledge of the inner surface of the hollow body, such that the spring extends coaxial to the poppet body. An o-ring may be coupled to the second end of the poppet. The valve assembly is configured to hold the poppet in tension by the spring disposed between the first end of the poppet and the ledge of the inner surface of the hollow body, such that the o-ring and the second end of the poppet seal the hollow body at the valve seat.

Figure 5:
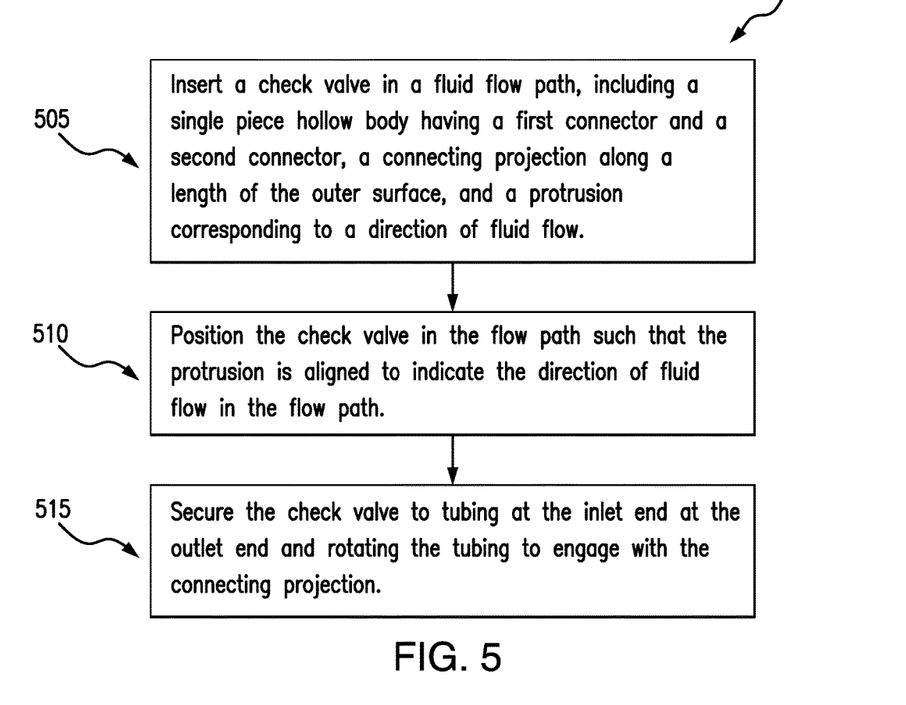
FIG. 5 illustrates a flow diagram of a method of operating a check valve according to an embodiment of the present invention.

FIG. 5 shows a flow diagram 500 of a method of operating a check valve according to an embodiment of the present invention. At step 505, the method may include inserting the check valve in a fluid flow path. The check valve may include a single piece hollow body having an inlet end and an outlet end. The inlet end may have a first connector and the outlet end may have a second connector. The single piece hollow body may further include a connecting projection disposed along a length of an outer surface, and a protrusion extending from the outer surface, the protrusion corresponding to a direction of fluid flow. At step 510, the method may further include positioning the check valve in the flow path such that the protrusion is aligned to indicate the direction of fluid flow in the flow path. At step 515, the method may further include securing the check valve to tubing at the inlet end and the outlet end by inserting the first connector at the inlet end and the second connector at the outlet end into the tubing, and rotating the tubing to engage with the connecting projection.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A check valve, comprising:
a hollow body, the hollow body including:
an inlet end;
an outlet end disposed opposite the inlet end, the inlet end having a first connector and the outlet end having a second connector;
connecting projections disposed along a length of an outer surface between the first connector at the inlet end and the second connector at the outlet end;
a protrusion extending from the outer surface, the protrusion corresponding to a direction of fluid flow; and
a sacrificial anode, wherein the sacrificial anode is a washer, the washer being configured to corrode at a rate faster than a spring disposed in the hollow body, and wherein the spring is formed of a first material and the washer is formed of a second material, the first material being different from the second material.

2. The check valve according to claim 1, wherein the outlet end of the hollow body includes a valve seat on an inner surface of the hollow body.

3. The check valve according to claim 2, further comprising a valve assembly, the valve assembly including:
a poppet disposed in the hollow body, the poppet having a first end disposed towards the inlet end, a second end disposed at the valve seat, and a poppet body extending between the first end of the poppet and the second end of the poppet;
the spring disposed in the hollow body, the spring having a first end coupled to the first end of the poppet and a second end disposed on a ledge of the inner surface of the hollow body, the spring extending coaxial to the poppet body; and
an O-ring coupled to the second end of the poppet;
wherein the spring is disposed between the first end of the poppet and the ledge of the inner surface of the hollow body, such that the O-ring and the second end of the poppet seal the hollow body at the valve seat.

4. The check valve according to claim 3, wherein the spring is formed of a first material, and the poppet is formed of a second material, the first material being different from the second material, and wherein the poppet is configured to corrode at a rate faster than the spring.

5. The check valve according to claim 3, wherein the O-ring is configured with respect to the valve assembly, such that the fluid flow exiting the check valve forms a quick spray against the valve seat in a self-cleaning manner.

6. The check valve according to claim 1, wherein the first connector and the second connector are barbs, each tapered in diameter from the protrusion outward to the outlet end and inlet end.

7. The check valve according to claim 1, wherein the connecting projections are a self-tapping screw thread.

8. The check valve according to claim 1, wherein the protrusion is a frustoconical protrusion, the frustoconical protrusion including a first diameter disposed towards the inlet end and a second diameter disposed towards the outlet end, the first diameter being larger than the second diameter.

9. The check valve according to claim 1, wherein the hollow body is a single piece hollow body.

10. A check valve, comprising:
   a hollow body, the hollow body including:
      an inlet end;
      an outlet end, the inlet end having a first connector and the outlet end having a second connector, wherein the outlet end of the hollow body includes a valve seat on an inner surface of the hollow body;
      connecting projections disposed along a length of an outer surface; and
      a protrusion extending from the outer surface, the protrusion corresponding to a direction of fluid flow;
   a valve assembly, the valve assembly including:
      a poppet disposed in the hollow body, the poppet having a first end disposed towards the inlet end, a second end disposed at the valve seat, and a poppet body extending between the first end of the poppet and the second end of the poppet;
      a spring disposed in the hollow body, the spring having a first end coupled to the first end of the poppet and a second end disposed on a ledge of the inner surface of the hollow body, the spring extending coaxial to the poppet body; and
      an O-ring coupled to the second end of the poppet;
   wherein the spring is disposed between the first end of the poppet and the ledge of the inner surface of the hollow body, such that the O-ring and the second end of the poppet seal the hollow body at the valve seat; and
   a sacrificial anode, wherein the sacrificial anode is a washer, the washer being configured to corrode at a rate faster than the spring, and wherein the spring is formed of a first material and the washer is formed of a second material, the first material being different from the second material.

11. A check valve, comprising:
   a single piece hollow body configured for a fluid flow from an inlet end to an outlet end, the outlet end including a valve seat on an inner surface;
   a spring disposed in the single piece hollow body;
   a poppet disposed in the single piece hollow body, the poppet having a first end coupled to the spring and a second end disposed at the valve seat, the poppet extending coaxial to the spring such that the poppet is held in tension by the spring;
   a sacrificial anode washer disposed at an end of the spring, the sacrificial anode washer being configured to corrode at a rate faster than the spring; and
   an O-ring disposed at the valve seat and coupled to the second end of the poppet;
   wherein the single piece hollow body includes connecting projections disposed along a length of an outer surface;
   wherein the spring is formed of a first material, and the sacrificial anode washer is formed of a second material, the first material being different from the second material.

12. The check valve according to claim 11, further comprising a first barb at the inlet end and a second barb at the outlet end, wherein the first barb and the second barb include a tapered outer surface projection, the projection extending from the outer surface of the single piece hollow body.

13. The check valve according to claim 12, wherein the first barb is configured to secure to tubing, and the second barb is configured to secure to tubing.

14. The check valve according to claim 11, wherein the single piece hollow body includes a flange disposed on the outer surface, the flange having an angled surface relative to the outer surface corresponding to a direction of fluid flow from the inlet end to the outlet end of the check valve.

15. The check valve according to claim 14, wherein the angled surface of the flange is a frustoconical shape, the frustoconical shape having a first diameter disposed towards the inlet end of the single piece hollow body, and a second diameter disposed towards the outlet end of the single piece hollow body, the first diameter being larger than the second diameter.

16. The check valve according to claim 11, wherein in response to a pressure of the fluid flow from the inlet end to the outlet end exceeding the tension of the spring, the spring is configured to compress such that the second end of the poppet and the O-ring unseal the valve seat for the fluid flow to exit the check valve.

17. The check valve according to claim 16, wherein the O-ring is configured with respect to a valve assembly including the poppet and the spring, such that the fluid flow exiting the check valve forms a quick spray against the valve seat in a self-cleaning manner.

18. The check valve according to claim 11, wherein the spring has a first end coupled to the first end of the poppet, and a second end disposed on a ledge of the inner surface of the single piece hollow body.

19. A method of operating a check valve, the method comprising:
   inserting the check valve in a flow path, the check valve including:
      a single piece hollow body, the single piece hollow body including:
         an inlet end;
         an outlet end disposed opposite the inlet end, the inlet end having a first connector and the outlet end having a second connector,
         connecting projections disposed along a length of an outer surface between the first connector at the inlet end and the second connector at the outlet end;
         a protrusion extending from the outer surface, the protrusion corresponding to a direction of fluid flow; and
         a sacrificial anode, wherein the sacrificial anode is a washer, the washer being configured to corrode at a rate faster than a spring disposed in the hollow body, and wherein the spring is formed of a first material and the washer is formed of a second material, the first material being different from the second material;
   positioning the check valve in the flow path such that the protrusion is aligned to indicate the direction of fluid flow in the flow path; and
   securing the check valve to tubing at the inlet end and the outlet end by inserting the first connector at the inlet end and the second connector at the outlet end into the tubing, and rotating the tubing to engage with the connecting projections.

* * * * *